(12) United States Patent
Kaplan et al.

(10) Patent No.: US 8,631,679 B2
(45) Date of Patent: Jan. 21, 2014

(54) ADDITIONAL CALIBRATION FOR ANALYTE MONITOR

(75) Inventors: Daniel Kaplan, Portland, OR (US); W. Kenneth Ward, Portland, OR (US)

(73) Assignee: iSense Corporation, Wilsonville, OR (US)

(*) Notice: Subject to any disclaimer, the term of this patent is extended or adjusted under 35 U.S.C. 154(b) by 581 days.

(21) Appl. No.: 12/554,830

(22) Filed: Sep. 4, 2009

(65) Prior Publication Data

US 2011/0056264 A1    Mar. 10, 2011

(51) Int. Cl.
*G01N 33/48* (2006.01)
(52) U.S. Cl.
USPC .......................................................... 73/1.02
(58) Field of Classification Search
None
See application file for complete search history.

(56) References Cited

U.S. PATENT DOCUMENTS

| | | | |
|---|---|---|---|
| 5,791,233 A | 8/1998 | Knapp | |
| 6,421,847 B2 | 7/2002 | Mastrototaro et al. | |
| 6,931,327 B2 | 8/2005 | Goode, Jr. | |
| 7,276,029 B2 | 10/2007 | Goode, Jr. | |
| 7,336,984 B2 | 2/2008 | Gough | |
| 7,384,397 B2 | 6/2008 | Zhang | |
| 7,494,465 B2 | 2/2009 | Brister | |
| 7,519,408 B2 | 4/2009 | Rasdal | |
| 2006/0036141 A1 | 2/2006 | Kamath et al. | |
| 2006/0281985 A1 | 12/2006 | Ward | |
| 2007/0016381 A1 | 1/2007 | Kamath | |
| 2007/0135696 A1 | 6/2007 | Ward | |
| 2008/0161666 A1 | 7/2008 | Feldman | |
| 2008/0228055 A1 | 9/2008 | Sher | |
| 2008/0270039 A1 | 10/2008 | Dunn | |
| 2009/0069655 A1* | 3/2009 | Say et al. | 600/347 |
| 2009/0101498 A1 | 4/2009 | Papadimitrakopoulos | |
| 2010/0213082 A1* | 8/2010 | Feldman et al. | 205/777.5 |
| 2010/0241388 A1* | 9/2010 | Say et al. | 702/104 |

* cited by examiner

*Primary Examiner* — Robert R Raevis
(74) *Attorney, Agent, or Firm* — Schwabe, Williamson & Wyatt, P.C.

(57) ABSTRACT

Embodiments provide a method and related systems that take into account the difference between a measured glucose value and the calibration level and the amount of elapsed time since the prior calibration. As one or both of these determined differences increases, the desirability of an additional calibration also increases. The methodology described herein thus analyzes the combination of change in glucose level as well as the time since the prior calibration. If the combination exceeds a predetermined value, the system recommends, but does not require, that the subject user perform an additional calibration.

22 Claims, 3 Drawing Sheets

ADDITIONAL CALIBRATION FOR ANALYTE MONITOR

TECHNICAL FIELD

Embodiments herein relate to the field of analyte monitoring, and, more specifically, to methods of calibrating an analyte monitor.

BACKGROUND

Among the other unpleasant aspects of having the disorder diabetes mellitus is the need to frequently test one's blood glucose concentration. With current technology a diabetic individual generally must prick his own fingertip or other body part to withdraw blood to determine the blood glucose concentration. The user may be informed directly of the blood glucose value, or the value may be used to calibrate a related device, such as a continuous glucose monitor. But, with the passage of time, continuous glucose monitors often become less accurate.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
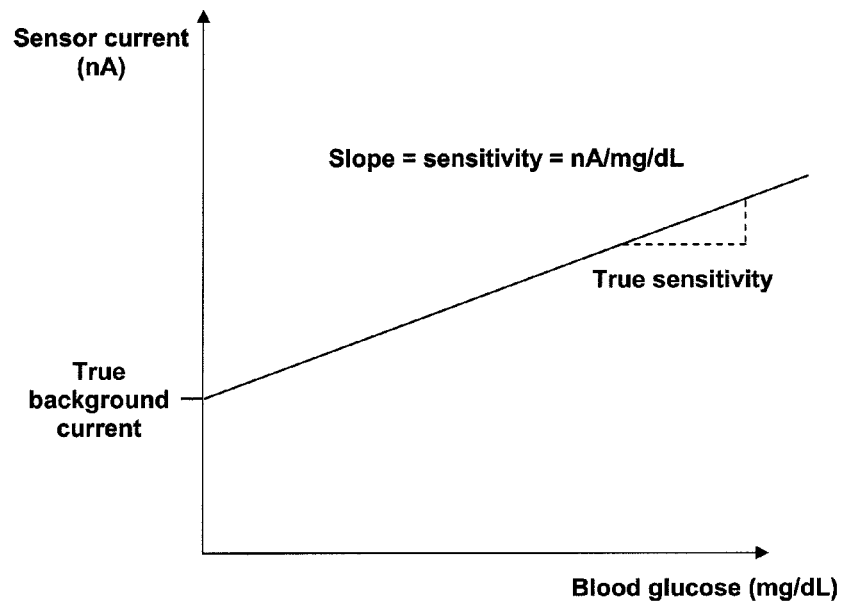
FIG. 1 is a graph illustrating sensor sensitivity.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems for calibrating an analyte monitor are provided. In exemplary embodiments, a computing device may be endowed with one or more components of the disclosed apparatuses and/or systems and may be employed to perform one or more methods as disclosed herein.

In embodiments, the monitored analyte may be any of one or more analytes, such as glucose, lactate, oxygen, etc. Various devices may be used to monitor the analyte value to determine a current status condition, identify changes, and/or alert the user of trends or problem conditions that may be developing. Such devices typically need to be calibrated to ensure the values derived from the devices are accurate and may be relied upon.

Calibration refers generally to a correction or validation of the measurements obtained by a particular device. For the purposes herein, calibration provides a comparison between measurements from a device providing a known value or a value having a more generally accepted accuracy with measurements from a device providing an unknown value or a value having a less accepted accuracy.

As an example, using a continuous glucose monitor (CGM), calibration is typically performed by first obtaining a blood glucose value via a fingerstick (blood droplet extracted from an individual and evaluated, for example, using a test strip and a blood glucose meter). The fingerstick derived blood glucose value may be assumed to be the glucose value that should be derived from the CGM sensor at approximately the same time, and thus the signal (sensor current) from the CGM sensor may be correlated to that fingerstick derived blood glucose value.

In a CGM, the sensor sensitivity indicates the change in sensor current value that is detected based on a change in the blood glucose value. Calibration is used to determine the sensor sensitivity value.

FIG. 1 is a graph illustrating exemplary blood glucose sensor sensitivity. The sensor current is plotted against the blood glucose value. The slope of the line extending from the true background current level identifies the sensitivity of the sensor measured in nA/mg/dL. As indicated in FIG. 1, some amount of background current is present, thus the sensor current is greater than zero even with a zero blood glucose value. Background current refers to the amount of current present or detected by the analyte monitor at a zero glucose level. Accounting for the background current is an important factor to ensure an accurate evaluation of the sensor sensitivity. At the time of calibration, the sensor glucose value is set equal to the blood glucose value, while accounting for the determined or selected background current value.

In analyte monitors, such as a CGM, two major sources of error are sensor drift and an incorrect estimation of the background current. Drift means that the sensitivity of the sensor changes over time. Sensor drift causes the sensitivity of the sensor to decrease in accuracy by becoming more or less sensitive over time. In addition, since in-vivo background current is not well predicted in-vitro, a single predetermined value is generally used for a population of sensors. Thus, some amount of incorrect estimation of background current is common. Calibration is designed to address both of the above-described sources of error.

Sensor error drift is minimized immediately after calibration but generally increases over time. Thus, the more time that elapses since the prior calibration, the greater the sensor error due to drift.

An incorrect estimation of background current, also referred to as calibration error, is an error caused by mis-identification of analyte current as background current or mis-identification of background current as analyte current. This error may be minimized if the analyte level at which accuracy is measured is close to the analyte level at which calibration is performed. Thus, assuming some amount of incorrect estimation of background current, the farther the analyte value travels away from the level at which calibration was carried out, the greater the calibration error.

Figure 2:
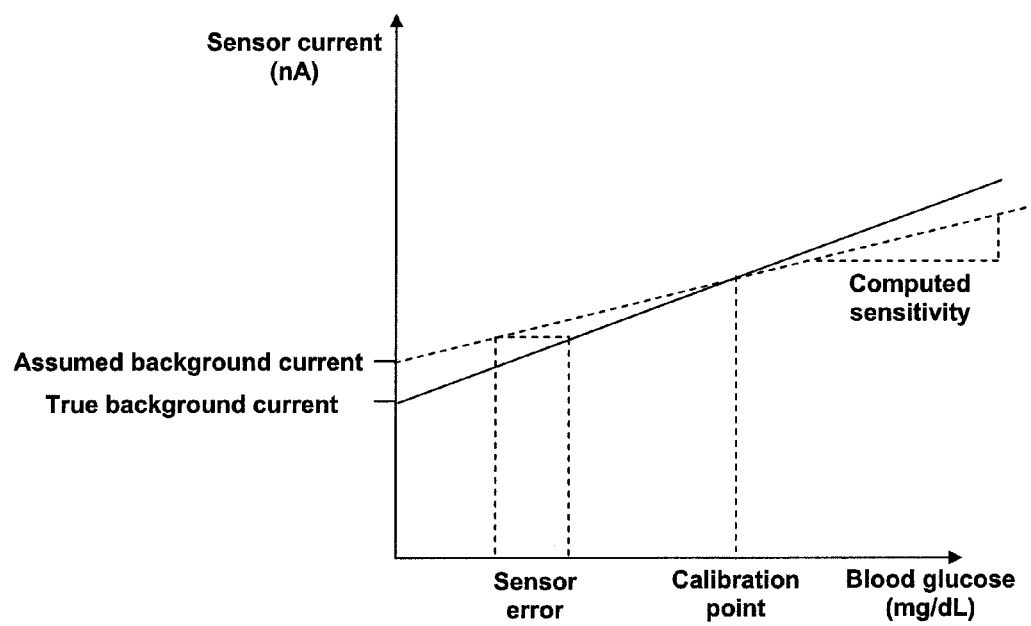
FIG. 2 is a graph illustrating computed sensitivity and the effect of error on such computations.

FIG. 2 is a graph illustrating computed sensitivity and the effect of error on such computations. In particular, FIG. 2 illustrates the impact of an incorrect estimation of the background current on the computed sensitivity of the sensor. The assumed background current in this example is higher than the true background current, and thus the computed sensitivity of the sensor introduces error into the determined blood glucose value.

Thus, an embodiment herein provides a method that takes into account the difference between a measured glucose value and the calibration level and the amount of elapsed time since the prior calibration. As one or both of these determined differences increases, the desirability of an additional calibration also increases. The methodology described herein thus analyzes the combination of change in glucose level as well as the time since the prior calibration. If the combination exceeds a predetermined value, the system recommends, but does not require, that the subject user perform an additional calibration.

Thus, a method is provided comprising determining by an analyte monitoring system a change in analyte value since a prior calibration; providing a change in analyte value threshold as a function of time elapsed since the prior calibration; determining by the analyte monitoring system whether the change in analyte value as a function of time exceeds the threshold; and if the change in analyte value as a function of time exceeds the threshold, providing by the analyte monitoring system an indication of that determination.

Calibrations are generally recommended on a predetermined time sequence, such as every 12 hours. Thus, periodically, such as every 12 hours, a user may be directed/prompted to perform a calibration. An analyte monitor may be programmed to provide an indication of the expiration of a set time period and/or the need/recommendation to calibrate.

Embodiments herein thus provide a method for indicating the desirability of or need for an additional "out of sequence" calibration of an analyte monitor based on one or more identified factors. Methods herein impart an increase in analyte sensor accuracy, with minimal inconvenience to the user.

The determination of whether or not a change in analyte value as a function of time exceeds a threshold may be made continuously or near continuously after a calibration. For example, such a determination may be made once every minute. Or, the determination may be made at longer periodic intervals after calibration, such as once every 10, 20, or 30 minutes.

In embodiments, an indication that a change in analyte value as a function of time exceeds a threshold may be made if one or a series of consecutive measurements/calculations indicates that the threshold has been exceeded. For example, the system may be configured to indicate that the threshold has been exceeded only if the threshold has been exceeded for a certain number of measurements/calculations, such as 5 or 10 measurements/calculations consecutively, or for a certain amount of time, such as consistently for a period of 10 or 15 minutes.

As an example, most users of continuous glucose monitoring systems already perform fingersticks (blood glucose measurements for calibration of the sensor). The general user operation is the same before and after introduction of this methodology. However, the new methodology would, in certain situations, increase the frequency with which a user performs, or at least is recommended to perform, blood glucose measurements to maintain a desired level of sensor accuracy.

In an exemplary method using glucose as the analyte, one may determine the change in glucose ($\Delta G$) since calibration as a function of $\Delta T$ (time since calibration). If $\Delta G$ exceeds the value prescribed by the function, an additional calibration may be indicated and/or recommended. Other analytes may be evaluated in a similar manner.

Figure 3:
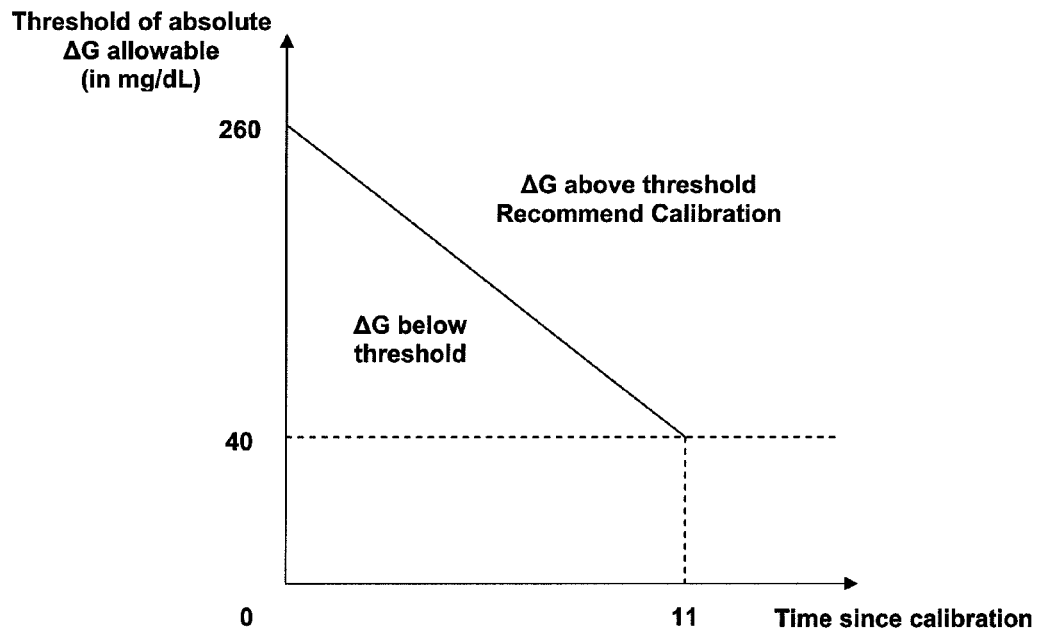
FIG. 3 is a graph showing a threshold and illustrating that an additional calibration recommendation may be defined as a linear function of both time since prior calibration and change in glucose value since calibration.

FIG. 3 illustrates an exemplary graph showing a threshold and illustrating that an additional calibration recommendation may be defined as a linear function of both time since prior calibration and change in glucose value since calibration. As indicated in this example, a change in glucose value of greater than +/−260 mg/dL results in a recommendation for an additional calibration. Whereas a change in glucose value of +/−40 mg/dL will not result in a recommendation for an additional calibration unless 11 hours have elapsed since the prior calibration.

While FIG. 3 shows a straight line (linear relationship) representing the additional calibration threshold, other relationships may be defined. In embodiments, a line may be replaced by any parameterized curve or function that describes the relationship between maximum allowed change in glucose since calibration (function, y-axis) and the maximum allowable elapsed time since calibration (coordinate, x-axis). The exact parameters of the curve/function may vary in order to optimize the sensor performance and balance the performance with being relatively unobtrusive, i.e. obtaining maximum performance gain for the minimum number of additional calibrations.

Figure 4:
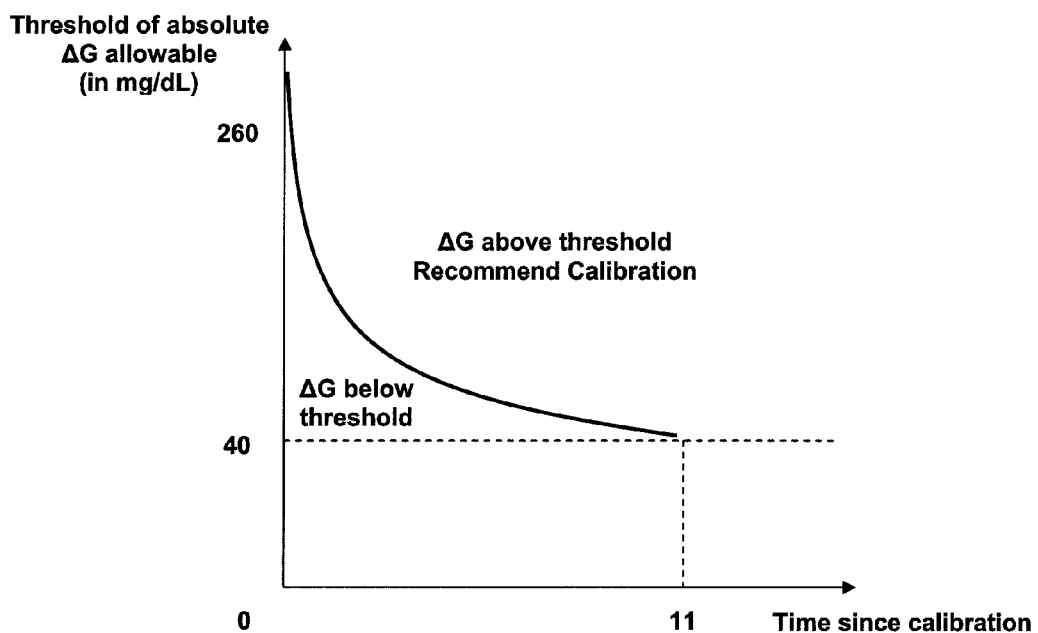
FIG. 4 is a graph showing a threshold and illustrating that an additional calibration recommendation may be defined as a non-linear function of both time since prior calibration and change in glucose value since calibration.

FIG. 4 illustrates an exemplary graph showing a threshold and illustrating that an additional calibration recommendation may be defined as a non-linear function of both time since prior calibration and change in glucose value since calibration.

The details provided in FIGS. 3 and 4 may be modified as desired in accordance with teachings herein. For example, the offset and/or $\Delta T$ threshold may be changed, as desired. Similarly, exemplary algorithms may be defined in accordance with the above-description using predetermined slope/curve, offset, and time parameters, which may be established as desired.

Figure 5:
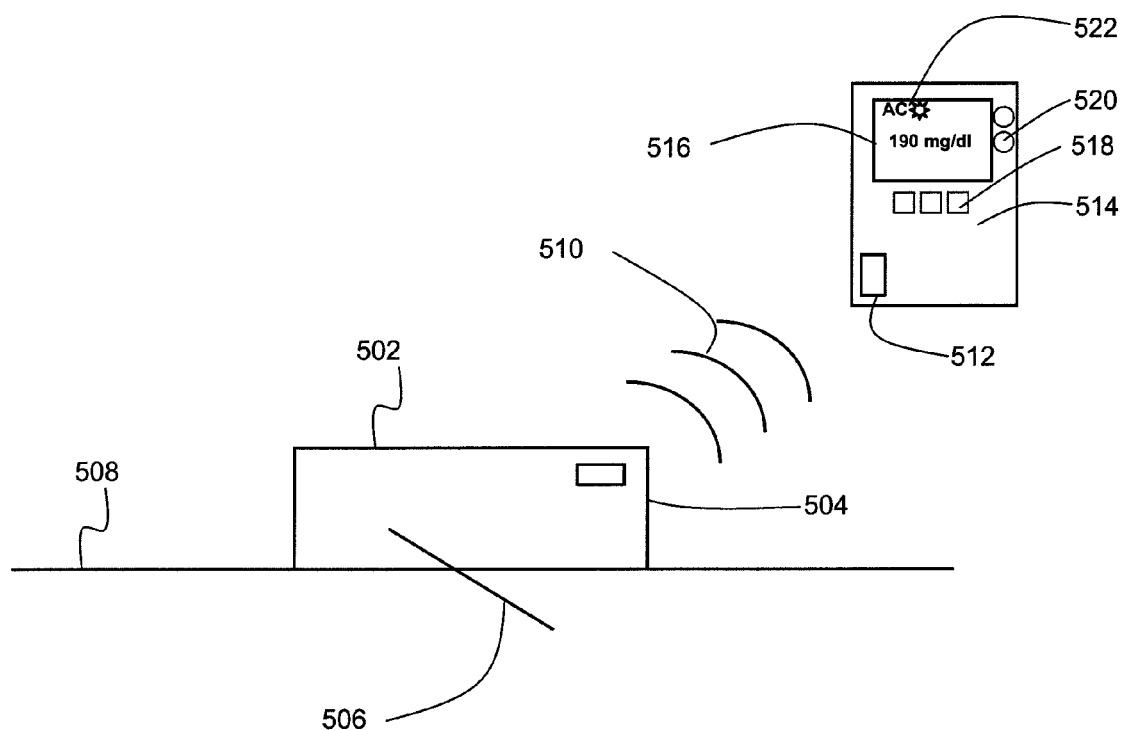
FIG. 5 illustrates an exemplary analyte monitoring system incorporating the methodology described herein.

FIG. 5 illustrates an exemplary analyte monitoring system incorporating the methodology described herein. In FIG. 5, an on-skin unit 502 contains various electrical components such as transmitter 504. Extending from and electrically coupled to on-skin unit 502 is analyte sensor 506 which has been inserted into skin 508 of an individual. As analyte sensor 506 obtains analyte values or representative values thereof, that information may be conveyed to on-skin unit 502 and transmitted (510) by transmitter 504 to a receiver 512 in an electronic monitoring unit 514. Various information regarding the obtained values or calculations associated therewith may be displayed on a display 516 of electronic monitoring unit 514. Unit 514 may contain one or more processors or other such devices to enable determinations regarding calibration, analyte value, trends, alarms, alerts, etc.

Unit 514 includes one or more buttons 518 that may be used to input information into unit 514, such as for the purpose of calibration. Unit 514 may also include an integrated blood glucose meter (not shown) to streamline the calibration process. As shown, unit 514 also includes one or more indicators 520 that may be used to indicate one or more conditions, such as a power state, a warning, etc.

Display 516 may provide one or more lights, indicators, icons, textual/numerical/graphical/pictorial representations of data, etc. As illustrated, display 514 may include one or more indicators 522, whether as text, graphics, etc., that recommend to a user to perform an additional calibration.

In embodiments, various types of notifications, such as alarms or alerts, may be used to indicate a current condition, especially a condition of concern or a recommendation, such as an audible (alarm or electronic voice prompt), visual (for example colored or flashing lights or a symbol on the display), and/or vibratory notification. In an embodiment, a notification may provide an indication of the degree of risk or the condition of concern. In an embodiment, a notification may also provide an indication or suggestion of an action to be taken as a result of the condition of concern, such as performing an additional calibration.

To illustrate the impact of the methodology described herein, data was collected in an exemplary home-use study. The users (subjects) were given a glucose monitoring system and instructed to perform their usual daily activities, while keeping a log of relevant activities (food and insulin intake, exercise, showers, etc.) and performing 5-8 fingersticks a day. The fingersticks may be used in later analysis for either calibration or evaluation. The data was analyzed retroactively, i.e. after the study's completion. The settings of the additional calibration algorithms were chosen in a way that provided the greatest boost to accuracy while requiring the least number of additional calibrations (i.e. above the necessary two calibrations per day).

With all other data parameters remaining unchanged, utilizing the additional calibration methodology described herein improved accuracy by ~1% MeanARD (for glucose values >70 mg/dL) and 6.4 mg/dL MeanAD (for glucose values <70 mg/dL). The method increased the number of calibrations from 2 per day to 2.6 per day, on average. Thus, a modest increase of 4 calibrations per week offered a significant increase in accuracy. It should be noted that in this study, the blood glucose measurements (i.e., the calibration times) could not be fully controlled and, in some cases, a significant amount of time passed between a recommendation of an additional calibration, and the patient actually performing the additional calibration. Thus, the improvements witnessed may be even better provided patient response is more contemporaneous with the additional calibration indication/recommendation.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method, comprising:
   determining by an analyte monitoring system a change in analyte value since a prior calibration;
   determining by an analyte monitoring system a time elapsed since a prior calibration;
   providing a threshold for the change in analyte value, wherein the threshold is a function of the time elapsed;
   determining by the analyte monitoring system whether the threshold has been exceeded based on the change in analyte value and the time elapsed; and
   in response to determining that the change in analyte value exceeds the threshold, providing by the analyte monitoring system an indication of that determination, or in response to determining that the change in analyte value does not exceed the threshold, providing no indication by the analyte monitoring system that the change in analyte value exceeds the threshold.

2. The method of claim 1, wherein providing an indication comprises providing by the analyte monitoring system a recommendation to perform an additional calibration of the analyte monitoring system.

3. The method of claim 1, wherein the analyte monitoring system is a glucose monitoring system.

4. The method of claim 1, wherein the threshold defines a maximum allowable change in analyte value since the prior calibration.

5. The method of claim 1, wherein the threshold defines a maximum allowable elapsed time since the prior calibration.

6. The method of claim 1, wherein the threshold defines a line between a maximum allowable change in analyte value since the prior calibration and a maximum allowable elapsed time since the prior calibration.

7. The method of claim 1, wherein the threshold defines a parameterized curve or function between a maximum allowable change in analyte value since the prior calibration and a maximum allowable elapsed time since the prior calibration.

8. The method of claim 1, wherein providing no indication by the analyte monitoring system that the change in analyte value exceeds the threshold further comprises waiting a period of time before re-determining a change in analyte value since the prior calibration and re-determining whether the change in analyte value exceeds the threshold.

9. The method of claim 1, wherein the threshold defines a line with negative slope.

10. An electronic monitoring unit comprising,
    a telemetry component configured to receive signals representative of analyte values transmitted from an on-skin unit of an analyte monitoring system; and
    a processor configured to
      determine a change in analyte value since a prior calibration;
      determine a time elapsed since a prior calibration;
      provide a threshold for the change in analyte value, wherein the threshold is a function of the time elapsed;
      determine whether the threshold has been exceeded based on the change in analyte value and the time elapsed; and
      in response to determining that the change in analyte value exceeds the threshold, provide an indication of that determination, or in response to determining that the change in analyte value does not exceed the threshold, providing no indication by the analyte monitoring system that the change in analyte value exceeds the threshold.

11. The electronic monitoring unit of claim 10, further comprising a display operatively coupled to the processor.

12. The electronic monitoring unit of claim 11, wherein the processor configured to provide an indication comprises a processor configured to provide a recommendation to perform an additional calibration of the analyte monitoring system.

13. The electronic monitoring unit of claim 12, wherein the display includes one or more indicators configured to indicate the additional recommended calibration.

14. The electronic monitoring unit of claim 13, wherein the one or more indicators are at least one of a textual, graphical, numerical, and pictorial indicator.

15. The electronic monitoring unit of claim 10, wherein the threshold defines a line with negative slope.

16. An analyte monitoring system comprising:
an on-skin unit coupled to at least one analyte sensor;
an electronic monitoring unit comprising,
  a telemetry component configured to receive signals measured by the analyte sensor and transmitted from the on-skin unit; and
  a processor configured to
    determine a change in analyte value since a prior calibration;
    determine a time elapsed since a prior calibration;
    provide a threshold for the change in analyte value, wherein the threshold is a function of the time elapsed;
    determine whether the threshold has been exceeded based on the change in analyte value and the time elapsed; and
    in response to determining that the change in analyte value exceeds the threshold, provide an indication of that determination, or in response to determining that the change in analyte value does not exceed the threshold, providing no indication by the analyte monitoring system that the change in analyte value exceeds the threshold.

17. The analyte monitoring system of claim 16, wherein the analyte sensor is a glucose sensor.

18. The analyte monitoring system of claim 16, further comprising a display operatively coupled to the processor.

19. The analyte monitoring system of claim 18, wherein the processor configured to provide an indication comprises a processor configured to provide a recommendation to perform an additional calibration of the analyte monitoring system.

20. The analyte monitoring system of claim 19, wherein the display includes one or more indicators configured to indicate the additional recommended calibration.

21. The analyte monitoring system of claim 20, wherein the one or more indicators are at least one of a textual, graphical, numerical, and pictorial indicator.

22. The analyte monitoring system of claim 16, wherein the threshold defines a line with negative slope.

* * * * *